United States Patent [19]
Brauer

[11] Patent Number: 5,836,096
[45] Date of Patent: Nov. 17, 1998

[54] APPARATUS FOR ILLUMINATING MEDICAL DIAGNOSTIC IMAGING FILM WITH ENHANCED VIEWABILITY

[76] Inventor: William R. Brauer, 2420 Pasadena Blvd., Wauwatosa, Wis. 53226

[21] Appl. No.: 610,218

[22] Filed: Mar. 4, 1996

[51] Int. Cl.$^6$ .................................................. G02B 27/02
[52] U.S. Cl. .............................................. 40/361; 353/38
[58] Field of Search ............................ 40/361, 366, 367, 40/564, 577, 715, 716; 359/634; 353/38

[56] References Cited

U.S. PATENT DOCUMENTS

| | | | |
|---|---|---|---|
| 5,056,912 | 10/1991 | Hamada et al. | 353/38 |
| 5,150,138 | 9/1992 | Nakanishi et al. | 353/38 |
| 5,187,599 | 2/1993 | Nakanishi et al. | 359/41 |
| 5,313,726 | 5/1994 | Yaniv et al. | 40/361 |
| 5,315,330 | 5/1994 | Hamada | 353/31 |
| 5,381,187 | 1/1995 | Takamatsu et al. | 348/759 |
| 5,398,125 | 3/1995 | Willett et al. | 359/41 |
| 5,594,830 | 1/1997 | Winston et al. | 385/146 |

FOREIGN PATENT DOCUMENTS

| | | |
|---|---|---|
| 05089827 | 4/1993 | Japan . |
| 95134009 | 12/1995 | WIPO . |

OTHER PUBLICATIONS

Letter to the Editor: "Contrast and Signal–to–Noise Ratio in Radiographic Images," *Radiology*, vol. 188, No. 3. Letter from Kevin J. Robson, BSc, C. John Kotre, BSc,MSc, and Keith Faulkner, BSc, MSc, PhD (Sep. 1993) pp. 878–880.

Abildgaard & Notthellen; "Increasing Contrast When Viewing Radiographic Images," *Radiology*, Nov. 1992, 185:475–478.

Feder, "Where Repetition Is Exciting: 3M Is Betting on Tiny Shapes Tightly Packed," *New York Times*, Business Section, Nov., 1995.

"3M Brightness Enhancement Film (BEF)" (Supplied by 3M Company) Copyright 1993.

*Primary Examiner*—Cassandra H. Davis
*Attorney, Agent, or Firm*—Skarsten Law Offices S.C.

[57] ABSTRACT

View box apparatus is provided for illuminating a film containing a medical diagnostic image for radiologic observation and study. A light source is contained within the view box, at one end thereof, and a transparent plate is positioned at the other end for supporting the imaging film. A panel of material is positioned in the box between the light source and the transparent plate to diffuse light from the source, and one or more layers of a microprism film is positioned between the diffuser panel and the imaging film. The microprism film layer reflects light rays which are incident thereon at an angle less than a critical angle back into the view box, so that such light rays do not pass through the microprism film to illuminate the imaging film. Light rays incident upon the microprism film which are greater than the critical angle are refracted by the microprism film, to provide light for illuminating the imaging film having a solid angle which is much less than the solid angle of light from the diffuser. Accordingly, the microprism film serves to substantially reduce scatter, and thereby significantly improves resolution and contrast for an observer of the imaging film.

7 Claims, 4 Drawing Sheets

APPARATUS FOR ILLUMINATING MEDICAL DIAGNOSTIC IMAGING FILM WITH ENHANCED VIEWABILITY

BACKGROUND OF THE INVENTION

The invention disclosed and claimed herein generally pertains to improved view box apparatus, of the type used to illuminate a film containing a radiographic or other medical diagnostic image for viewing and study. More particularly, the invention pertains to apparatus of such type wherein the contrast and resolution, or sharpness, of a viewed image is significantly improved or enhanced, whereby viewability is improved.

As is well known, a view box, also known as a light box, is a device used by radiologists to view and study radiographic images and other medical diagnostic images which are on film. Such images, showing selected views of body tissue, can be obtained by means of conventional X-ray, computed tomography (CT), magnetic resonance imaging (MRI), and other techniques known to those of skill in the medical diagnostic imaging arts. By carefully studying such images, a radiologist can note the presence of significant medical conditions in a patient or other subject, without the need for invasive surgery. Some important examples of such conditions include breast cancer, lung cancer, pneumonia, fracture, and arthritis.

A conventional view box generally contains one or more fluorescent tubes or other sources of light, and has a front panel typically comprising a translucent light diffuser, such as a sheet of milky white plexiglass. The radiographic imaging film is placed on the light diffuser and transilluminated, for viewing and study, by light from the light source. The light passes through the diffuser and is diffused or scattered thereby. Thus, the light transmitted to the imaging film is of uniform brightness or intensity, so that the imaging film is uniformly illuminated.

If a view box was not provided with a diffuser or other means for scattering light from the fluorescent tube light source, the fluorescent tubes would tend to be seen through the imaging film, interfering with the study thereof. However, the scattering or diffusing of illuminating light causes contrast between lighter and darker regions on the imaging film, as well as resolution, to be degraded from the perspective of an observer.

More particularly, because the light which carries the film image to a viewer's eye is diffused, edges or boundaries between lighter and darker regions of the image are blurred, as received on the retina of the viewer. Thus, the radiologist's task of correctly interpreting a film image is made more difficult. Certain conditions, such as breast cancer, lung nodules, and small pneumothorax (collapsed lung) are especially hard to detect in any event. If there is too much blurring of edges, or insufficient contrast between lighter and darker areas of a film image, a correct diagnosis of such conditions may not even be possible. The term "resolution," as used herein, means the level of sharpness or blurring which characterizes the boundary, or edge, between adjacent lighter and darker regions of an image.

The importance of providing a high level of contrast and resolution, in illuminating a diagnostic imaging film, is further emphasized by certain regulations of the U.S. government. Under federal law, all X-ray equipment used in the United States for mammography, that is, for acquiring radiographic images for detecting breast cancer, must be periodically tested for contrast and resolution. Such test is conducted by producing a radiographic image of a standardized mammography phantom, which is analyzed by a federal inspector or medical personnel. If the inspector determines that contrast or resolution of the image is insufficient, the facility at which the equipment is located will not be allowed to perform further mammography until the situation is corrected. Such federal standards have been put into place because, if there is insufficient contrast between two adjacent areas of slightly different density in a breast, or insufficient resolution along the edge therebetween, a subtle breast cancer (characterized by an only slightly different density from surrounding normal breast tissue) will not be detectable. This, in turn, may result in a delay of treatment, which could cause great harm to a patient.

In the past, it has been suggested that contrast of a medical diagnostic imaging film, illuminated by means of a view box, could be improved by substantially increasing the spatial separation between the light source and the imaging film. Thus, the light illuminating the film would become less diffused i.e., the solid angle thereof, as described hereinafter in further detail, would decrease. However, the proposed spatial separation was on the order of six to twelve feet, whereas the depth of a conventional view box is generally less than one foot. It would be highly impractical for a number of reasons, including cost and spatial constraints, to construct a view box having the proposed expanded dimensions.

The inventor herein is not aware of any prior art relating decrease in diffusion of illuminating light to improvement in resolution.

SUMMARY OF THE INVENTION

The invention provides apparatus for illuminating a medical diagnostic imaging film, and includes means for supporting the imaging film in a specified plane. The invention further comprises means for projecting light toward the supported imaging film, the projected light having a first solid angle. A light directing film means is positioned between the imaging film and the light projecting means so that the projected light is incident on the light directing film means. The light directing film means selectively reflects and/or refracts at least a portion of the projected light to provide redirected light for illuminating the imaging film, the illuminating light having a second solid angle which is substantially less than the first solid angle. Preferably the light directing film means comprises one or more layers of a film having a number of microscopic prism elements, or microprisms, formed on one side.

The term "solid angle," as used herein is a measure of the divergence, diffusion, or scattering of a quantity of light, such as light projected toward, or illuminating the plane of the imaging film. The solid angle is oriented along an axis which is orthogonal to the film plane, and may vary from zero degrees, i.e., parallel light, to on the order of 180 degrees, i.e., very scattered or diffused light.

In a preferred embodiment, the light directing film means has an associated critical angle and is in parallel relationship with the specified plane. Some of the rays of the projected light, respectively directed along lines intersecting the specified plane at angles which are less than the critical angle, comprise a first portion of projected light. Other of said projected light rays, respectively directed along lines intersecting the specified plane at angles which are greater than the specified critical angle, comprise a second portion of projected light. The light directing film means prevents transmission of the first projected light portion to the imaging film, and refracts the second projected light portion, so that respective rays thereof are converged to lie within the second solid angle.

OBJECTS OF THE INVENTION

An object of the invention is to improve or enhance contrast and resolution provided by apparatus illuminating radiographic and other medical diagnostic imaging films for viewing.

Another object is to provide view box apparatus for diagnostic imaging film, wherein contrast and resolution are enhanced without significantly increasing cost or complexity over prior art view boxes.

Another object is to provide view box apparatus of the above type which substantially retains the dimensions of currently used view boxes.

Another object is to provide a view box of the above type which may be readily constructed by retrofitting, with comparative simplicity, a prior art view box.

These and other objects of the invention will become more readily apparent from the ensuing specification, taken together with the accompanying drawings.

DETAILED DESCRIPTION OF THE PREFERRED EMBODIMENT

Figure 1:
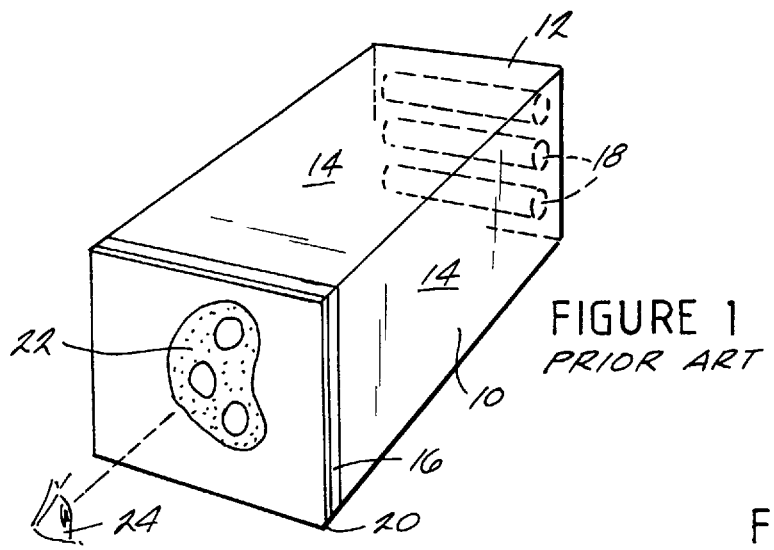
FIG. 1 is a perspective view showing a prior art view box.

Referring to FIG. 1, there is shown a conventional view box 10, generally comprising a rear wall 12, side walls 14, and a diffuser panel 16, which collectively enclose a space. Fluorescent tubes 18 are mounted on the inner surface of rear wall 12, to serve as a light source for the view box 10. Diffuser panel 16 comprises a sheet of translucent, milky white plexiglass, as described above, so that light from the source can pass through the diffuser panel, and be diffused or scattered thereby. An X-ray or radiographic film 20 is fastened upon diffuser 16 panel by clips or other suitable means (not shown), so that light transmitted through diffuser 16 illuminates an X-ray image 22 imprinted on the film 20. The light carries an image of the X-ray film image 22 to the retina 24 of an observer's eye.

Figure 2A:
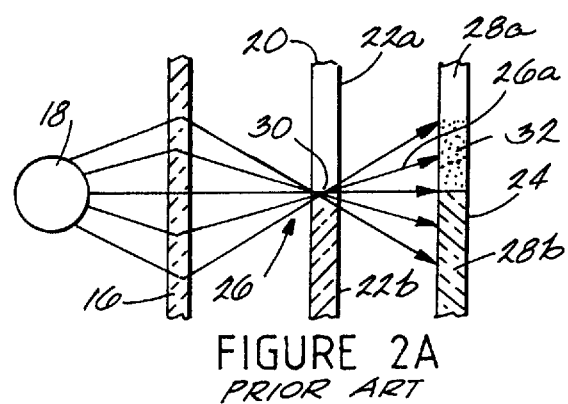
FIG. 2A is a diagram illustrating the effect of scattered light in transilluminating medical diagnostic imaging film.

Referring to FIG. 2A there is shown a portion of X-ray film 20, spaced apart from a portion diffuser panel 16, for purposes of illustration, although they are actually in abutting relationship as shown in FIG. 1. The portion of diffuser panel 16 receives light from fluorescent tubes 18, to project scattered or diffused light rays 26 toward X-ray film 20. A portion of the X-ray image 22, comprising lighter and darker regions 22a and 22b, respectively, is projected onto the retina 24 by the light rays 26, as lighter and darker images 28a and 28b, respectively corresponding to regions 22a and 22b.

Referring further to FIG. 2A, there is shown some of the scattered light rays 26 depicted as rays 26a, passing through film 20 at a boundary or edge 30 between lighter and darker portions 22a and 22b, to project an image 32 of the edge 30 onto the retina 24. However, because of the diffused nature of light rays 26a, the image 32 is a blurred representation of the edge 30, not a clear and sharp representation. Thus, resolution between X-ray image portions 22a and 22b is degraded, as stated above. Accordingly, it becomes more difficult to accurately interpret medical information provided by X-ray image 22.

Figure 2B:
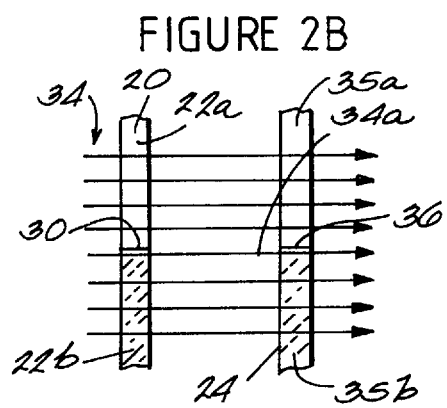
FIG. 2B is a diagram illustrating the effect of parallel light in transilluminating medical diagnostic imaging film.

Referring to FIG. 2B, there is shown X-ray film 20 transilluminated by light rays 34, having a solid angle which is much smaller than the solid angle of light rays 26. In one case, the solid angle could be on the order of zero degrees, so that all the rays 34 are in parallel relationship with one another. In such case, all the light rays 34 intersect the plane of film 20 at the same angle, such as 90 degrees, rather than at different angles varying over a wide range. The light rays 34 project regions 22a and 22b onto retina 24 as respectively corresponding images 35a and 35b, in similar manner to images 28a and 28b, described above. In addition, a portion of the light rays 34 which pass through edge 30 on film 20, represented in FIG. 2B as light ray 34a, project a sharp and unblurred image 36 of the edge 30 onto the retina 24. An observer is thereby able to much more clearly distinguish between light and dark regions 22a and 22b, indicating significant improvement in resolution and contrast.

Figure 3:
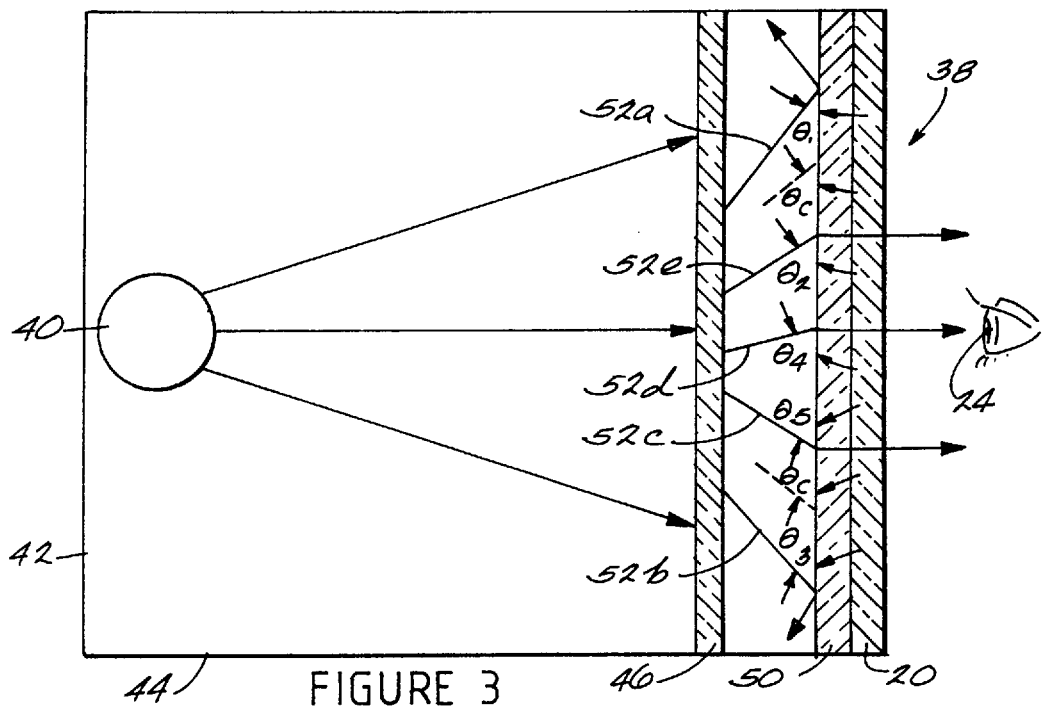
FIG. 3 is a side view showing an embodiment of the invention.

Referring to FIG. 3, there is shown a view box 38 generally comprising a light source 40, rear wall 42 and side walls 44, which are respectively similar or identical to fluorescent tubes 18 and walls 12 and 14 described above. The diffuser panel 46, similar or identical to diffuser 16, is positioned to diffuse light passing therethrough from the light source 40 to the front of view box 38, i.e., to the rightward side thereof as viewed in FIG. 3. FIG. 3 further shows a panel 48 in front of view box 38, usefully comprising tempered plate glass having a thickness on the order of one-sixteenth of an inch. The X-ray film 20, described above, is mounted on the glass panel 48 by suitable means (not shown).

Parallel light rays 34a, associated with a zero degree solid angle, generally provide the best level of resolution and contrast in illuminating a film. However, as described hereinafter, there are certain benefits in some applications in providing illuminating light which is non-parallel but still has an associated solid angle which is much less than the solid angle characterizing light rays 26.

In accordance with the invention, FIG. 3 further shows a film of light directing material 50 positioned across the front end of view box 38, between diffuser 46 and X-ray film 20, as hereinafter described. Preferably, film 50 is in abutting relationship with panel 48. Thus, all of the light transmitted through and diffused by diffuser 46 is incident upon the film 50, which is provided to improve resolution and contrast in viewing the image 22 on X-ray film 20, as hereinafter described.

Film 50 is selected to comprise a film material capable of directing incident light rays in accordance with a critical angle $\theta_c$ relative to the plane of film 50. More specifically, when light rays from diffuser 46 are incident on the film 50 at angles of incidence which are less than $\theta_c$, at least some of such light rays will be reflected by the film 50 back into the interior of view box 38, and will therefore not be transmitted through glass plate 48 to illuminate X-ray film 20. However, when other light rays from diffuser 46 are incident on the film 50 at angles of incidence are which greater than $\theta_c$, least some of such light rays will pass through the light directing film 50, but will be refracted thereby onto paths lying at much smaller angles relative to an axis orthogonal to the plane of film 50 than the angles of their respective paths prior to refraction. Thus, FIG. 3 shows incident light rays 52a and 52b reflected back from the film 50, since their respective angles of incidence $\theta_1$ and $\theta_3$ are less than the critical angle $\theta_c$. On the other hand light rays 52c, 52d, and 52e are each refracted by film 50 as described above, since their respective angles $\theta_5$, $\theta_4$ and $\theta_2$ are all greater than $\theta_c$. Accordingly, they are redirected or converged to lie within a smaller solid angle, prior to passing through plate 48 to transilluminate the X-ray image 22 to carry such image to retina 24. Resolution and contrast of the image received by the retina are thereby significantly improved, over an image provided by light having a substantial diffused component. Since the light ray directing film 50 and the X-ray film 20 respectively abut the parallel opposing faces of glass plate 48, the respective planes of films 50 and 20 are in parallel relationship.

It is to be understood that the degree of convergence of the refracted light rays 52c–e will depend upon the material selected for use as film 50. Accordingly, in one application the light rays 52c–e may be converged so that their respective refracted paths lie within a solid angle on the order of zero degrees. In such case, the rays 52c–e will be in parallel relationship with each other and orthogonal to the plane of film 20. In another application the light rays 52c–e may be converged so that their associated solid angle is on the order of 90 degrees.

It is to be further understood that varying amounts of scattered light, i.e., light not bounded by the solid angle of the redirected light, will pass through film 50, once again depending on the material selected therefor. Contrast and resolution of an illuminated imaging film 20 are generally improved by reducing the scattered light component of the film illuminating light, and also by reducing the solid angle of the redirected light component of the illuminating light.

FIG. 3 shows diffuser panel 46 spaced apart from light directing film 50, to the left as viewed in FIG. 3. In an alternative embodiment diffuser panel 46 could be in abutting relationship with the film 50. Also, it will be readily appreciated that film 50 acts to reduce the amount of light available from a given source 40 to illuminate X-ray film 20, since some of the light is reflected back into the view box as described above. Accordingly, it may become necessary to increase the intensity of the light source, such as by adding additional fluorescent tubes or a reflector thereto.

Figure 4:
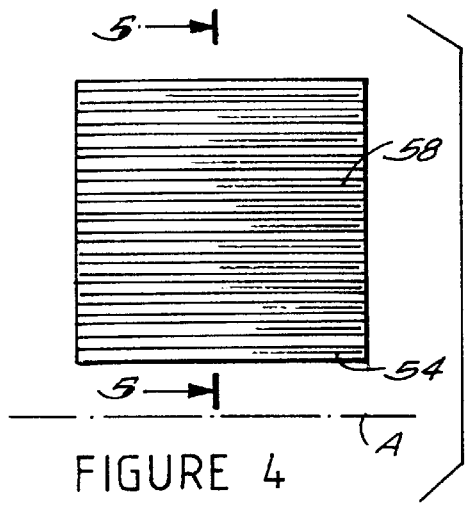
FIG. 4 shows a film material, comprising parallel rows of microprisms, which are usefully employed in the embodiment of FIG. 3.
Figure 5:
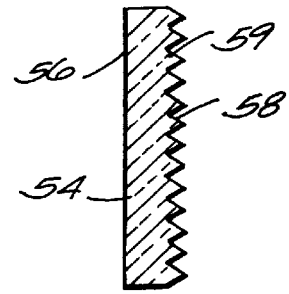
FIG. 5 is a sectional view taken along lines 5—5 of FIG. 4.
Figure 6:
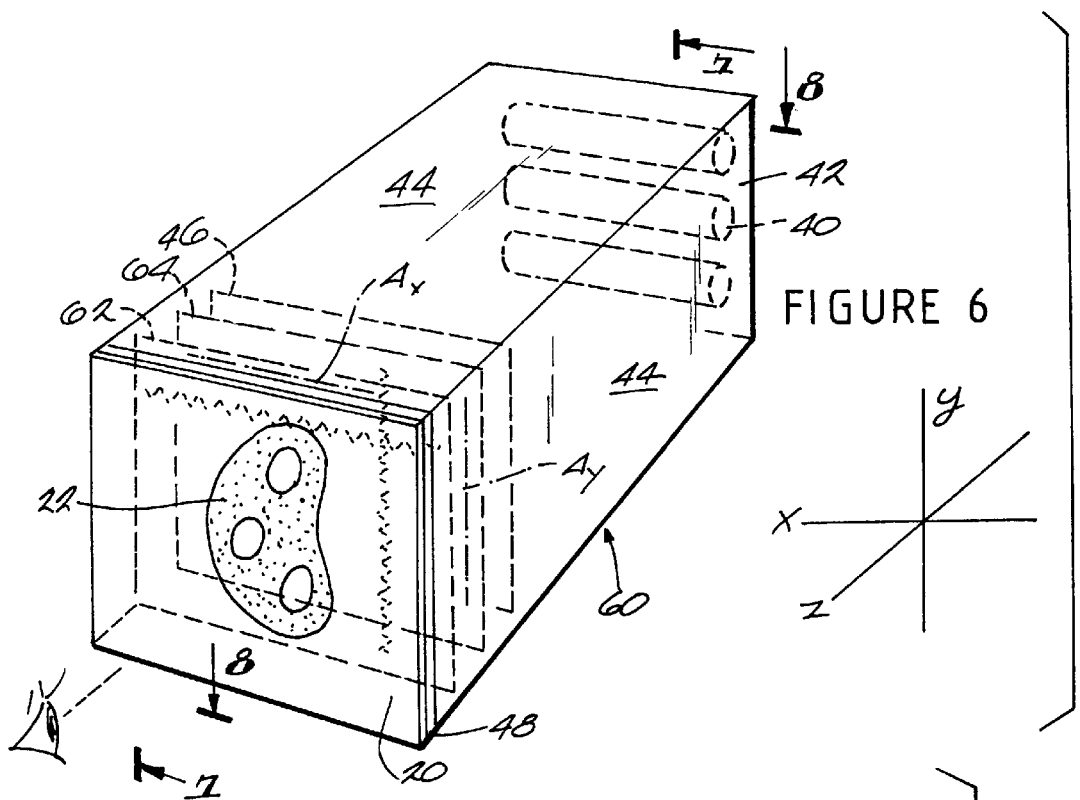
FIG. 6 is a perspective view showing a second embodiment of the invention.
Figure 7:
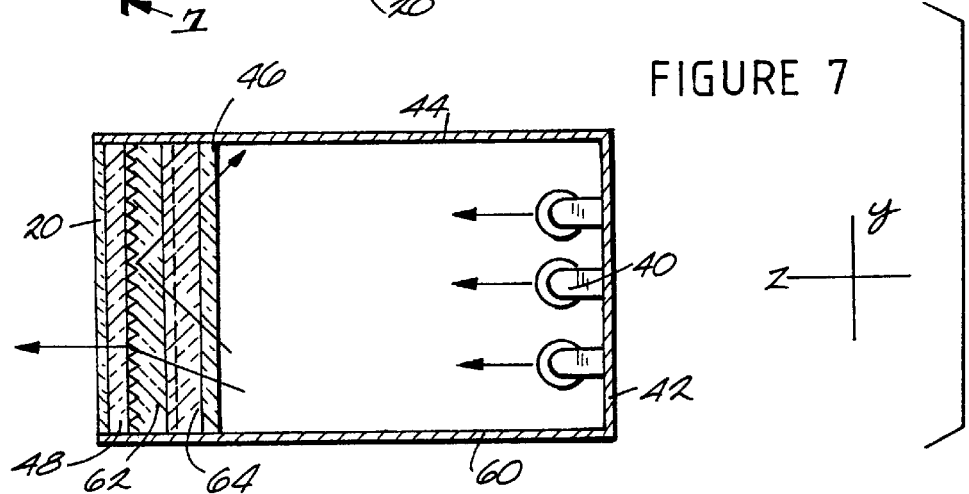
FIG. 7 is a view taken along lines 7—7 of FIG. 6.
Figure 8:
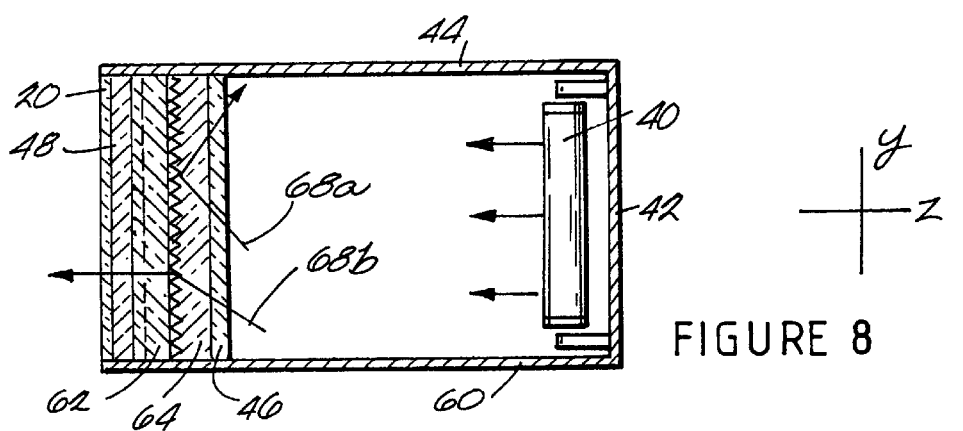
FIG. 8 is a sectional view taken along lines 8—8 of FIG. 6.

It is anticipated that different alternative film materials may be used for light directing film 50, to achieve the results set forth above. It has been found that a particularly useful material therefor comprises a product manufactured by the Minnesota Mining and Manufacturing Company and referred to as Brightness Enhancment Film. Referring to FIGS. 4 and 5 in combination, there is shown a sheet 54 of such film material, having a smooth side 56 and an opposing side having a large number of parallel microscopic ridges 58 formed therein. Each ridge 58 extends across the face of sheet 54, and has a triangular cross section 59 of microscopic size. Thus, each ridge 58 comprises a microprism. Such microprism film 54 has a thickness on the order of 0.1 mm, and a spacing on the order of 0.1 mm between the peaks of adjacent ridges 58. Hereafter, hypothetical reference axes, such as axis A shown in FIG. 4, are employed in connection with sheets of microprism film 54 to indicate the respective orientation of their parallel ridges 58. The ridges or microprisms 58 of film 54 are very effective in directing incident light rays as described above, which lie in, or have large components lying in planes orthogonal to the directions of the ridges. However, components of diffused light lying in other planes will tend to pass through the film 54 without change in direction. Accordingly, if microprism film 54 is used as light directing film 50, it has been found that two sheets of film 54, used as shown in FIG. 6, are more effective than a single sheet in reducing the scattered light component of the light illuminating X-ray film 20. Thus, FIG. 6 shows a view box 60 which has been modified from the view box 38, described above, by substituting two sheets of microprism film 54 for the single film 50. The two film sheets, respectively referenced in FIG. 56 as microprism films 62 and 64, have their microprism ridges respectively oriented in parallel relation with the axes $A_x$ and $A_y$. Films 62 and 64 are in parallel abutting relationship with each other, and with X-ray film 20, and are positioned between diffuser panel 46 and the glass plate 48, which supports X-ray film 20 as described above. The smooth sides 56 of microprism films 62 and 64 face toward the light source 40 and diffuser 46 of view box 60, as best shown in FIGS. 7 and 8. The microprism ridges 58 thereof are directed toward the X-ray film 20.

Referring further to FIG. 6, there is shown view box 60 oriented along the Z-axis of a rectangular coordinate system comprising orthogonal X, Y, and Z axes, for purposes of illustration. Films 62 and 64 are both parallel to the XY plane, and orthogonal to the Z axis. The reference axes $A_x$ and $A_y$ are respectively parallel to the X and Y axes, so that the microprism ridges 58 of film 62 are oriented at 90 degrees to the ridges of film 64. Thus, film 62 acts upon light rays which lie in or have substantial components lying in the X-Z plane, such as light rays 66a and 66b shown in FIG. 7. The film 62 reflects light rays 66a back into view box 60 since the incident angle thereof is less than the critical angle $\theta_c$. On the other hand, the incident angle of light rays 66 is greater than the critical angle $\theta_c$, so that light ray 66b is refracted by film 62 onto a path lying at a smaller angle, relative to an axis orthogonal to the plane of film 62, and therefore to the plane of X-ray film 20.

Similarly, film 64 acts upon light rays which lie in or have substantial components lying in the Y-Z plane, such as light rays 68a and 68b shown in FIG. 8. Film 64 reflects light ray 68a back into view box 60, and refracts light ray 68b onto a path lying at a smaller angle relative to an axis orthogonal to the plane of film 64 and to X-ray film 20.

Figure 9:
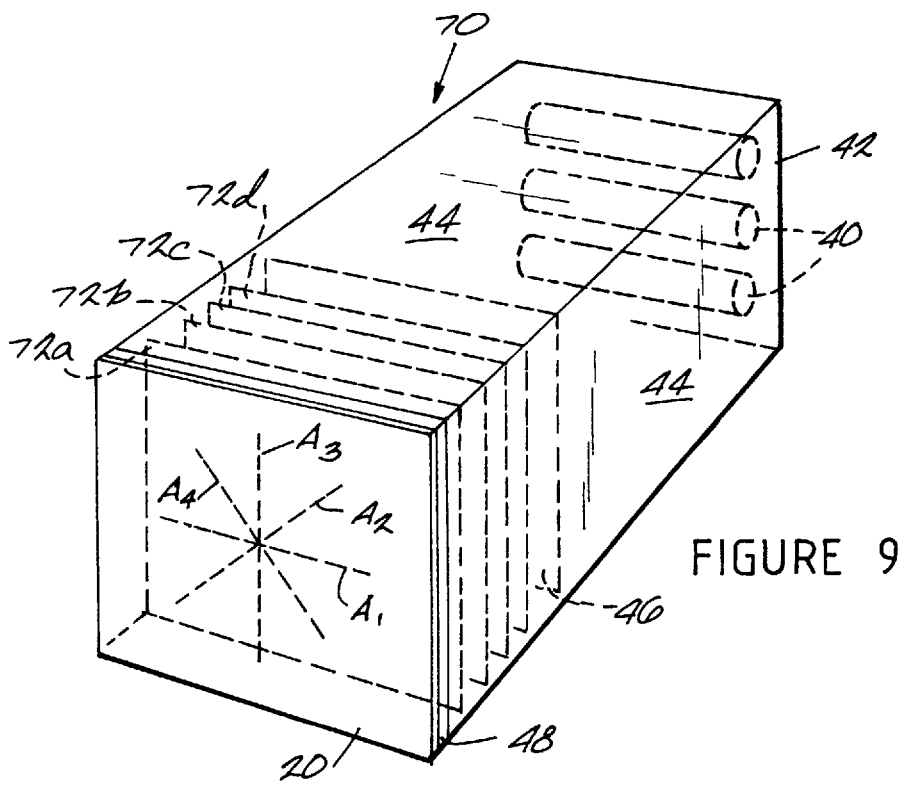
FIG. 9 is a perspective view showing a third embodiment of the invention.

Referring to FIG. 9, there is shown a view box 70, which has been modified from view box 38 by substituting four sheets or layers of microprism film 54, respectively referenced as film layers 72a–d, for the single film 50. As with film 62 and 64 of view box 60, film layers 72a–d are stacked together in abutting relationship between diffuser panel 46 and glass plate 48, supporting the X-ray film 20, and in parallel relation with each other and film 20. Respective film layers 72a–d are positioned in parallel relationship with the XY plane of a rectangular coordinate system, and in orthogonal relationship with the Z-axis thereof. Moreover, the film layers 72a–d are positioned so that their respective microprism ridges 58 are oriented or aligned at angles of 45 degrees with respect to one another. This is illustrated in FIG. 9, which shows the axis $A_1$ corresponding to film layer 72a oriented at an angle of zero degrees in relation to the X-axis. Axes $A_2$–$A_4$, respectively corresponding to film layers 72b–d are shown positioned around the Z-axis at 45 degrees, 90 degrees, and 135 degrees respectively, in relation to the X-axis.

It has been found that use of four microprism film layers, oriented as described above, is particularly effective in further reducing the component of scattered light which is able to pass therethrough to X-ray film 20. However, it has also been found that the total amount of light reaching X-ray film 20 through the microprism film layers 72a–d may be significantly reduced for a light source 40 of given intensity. Such loss of brightness may be readily compensated for, as stated above, by adding additional fluorescent tubes to the light source, or by adding a reflector behind the fluorescent tubes.

It is to be understood that if all light rays passing through a film 20 were perfectly parallel, i.e., if the solid angle thereof was zero degrees and there was no scattered light component, only a small part of the film could be seen. Another small part of the same film, or a different film to be viewed simultaneously, could be seen only if the observer moved his or her head. This would be impractical, since it is typically necessary to see all of the film, as well as another comparison film to make a diagnosis. For example, the American College of Radiology states that old mammogram images must be compared with new mammogram images to detect change, which can be a sign of cancer. An observer must be able to simultaneously see a given view of the breast on both old and new mammograms. Accordingly, while it is desirable to make the light illuminating the imaging film substantially parallel, to improve contrast and resolution as described above, it will frequently or usually be desirable to provide some divergence of the illuminating light rays, i.e., to have a solid angle greater than zero degrees. It is considered that the film illuminating light provided by the embodiments described above in connection with both FIG. 6 and 9 achieve the desired amount of divergence of light so as to produce increased contrast and resolution, while still providing simultaneous viewing of a large enough area of film.

Figure 10A:
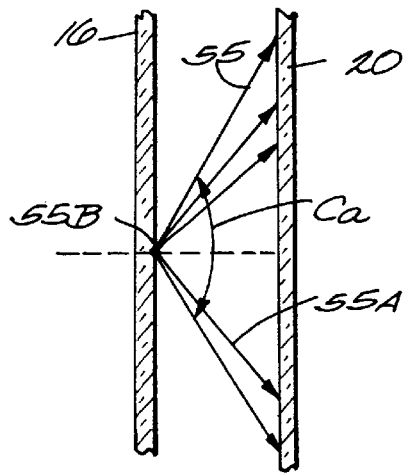
FIG. 10A is a diagram illustrating illumination of imaging film by means of light having a comparatively large solid angle.

Referring to FIG. 10A, there is shown solid angle 55, characterizing light projected toward film 20 from diffuser 16 of prior art view box 10. Solid angle 55 is oriented along an axis 57 in orthogonal relationship with the plane of film 20, and has a magnitude $C_a$. $C_a$ is extremely large, such as on the order of nearly 180 degrees. The edge of solid angle 55 is defined by very scattered light beams 55A, and the center of vertex 55B thereof, is located at a point on the edge of diffuser 16.

Figure 10B:
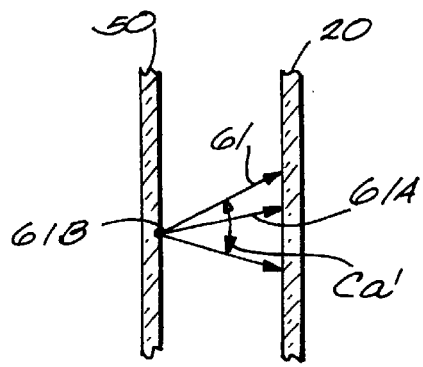
FIG. 10B is a diagram illustrating illumination of imaging film by means of light having a reduced solid angle.

Referring to FIG. 10B, there is shown solid angle 61 characterizing light projected to illuminate the film 20 which has been redirected by film 50, such as microprism film 54. Solid angle 61 is oriented along an axis 63 in orthogonal relationship with the plane of film 20, and has a magnitude $C'_a$, which is usefully on the order of 90 degrees. The edge of solid angle 61 is defined by light rays 61A, which are much narrower than rays 55A, and the vertex 61B is located at a point on the edge of film 50.

Figure 11:
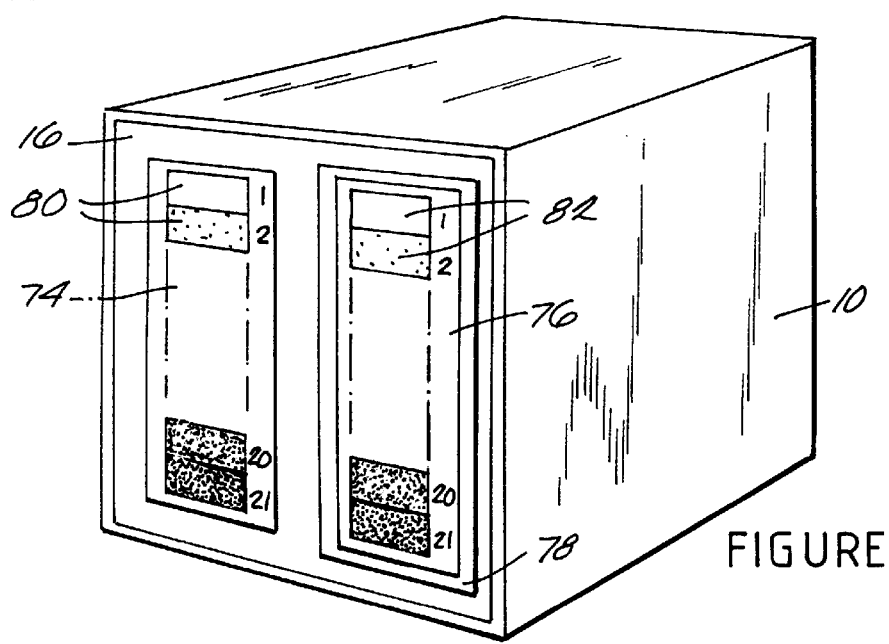
FIGS. 11 and 12 together show an arrangement used to compare contrast respectively provided by the embodiment shown in FIG. 9, and a view box of the prior art.

Referring to FIG. 11, there is shown an arrangement employed to quantitatively compare contrast in imaging films respectively illuminated by the embodiment shown in FIG. 9 and the prior art view box. FIG. 11 shows a conventional view box 10 as described above in connection with FIG. 1, except that light source 12 thereof has been replaced by a strobe light (not shown) having a thin cloth (not shown) placed over it, to act as an additional light diffusing mechanism. The combined effect of the strobe light, cloth, and diffuser panel 16 is to provide extremely even illumination for an X-ray or other photographic film placed upon the diffuser panel 16.

Referring further to FIG. 11, there are shown two identical gray scale step wedges 74 and 76, hereafter described, attached to diffuser panel 16 by suitable means (not shown). Step wedge 74 is attached directly to diffuser 16. A portion of the film layers 72a–d, described above in connection with FIG. 9 and shown in FIG. 11 as film layers 78, are positioned between diffuser panel 16 and step wedge 76. Thus, step wedge 74 is illuminated in accordance with the prior art whereas step wedge 76 is illuminated by the embodiment of the invention shown in FIG. 9.

Each of the step wedges 74 and 76 comprises a product well known in the art and formed from a piece of photographic film by sequentially exposing small, adjacent rectangular areas thereon, to increasing levels of light. This produces a row of small rectangles, or steps 80 and 82, respectively, each slightly darker than the adjacent previously exposed step. A typical step wedge includes twenty-one successively numbered steps, the first being transparent to light, and the twenty-first, or last, being opaque. It will be understood that wedges 74 and 76 are commercially available products, manufactured with a comparatively high level of precision for use in calibration and the like, and are selected to be identical.

Figure 12:
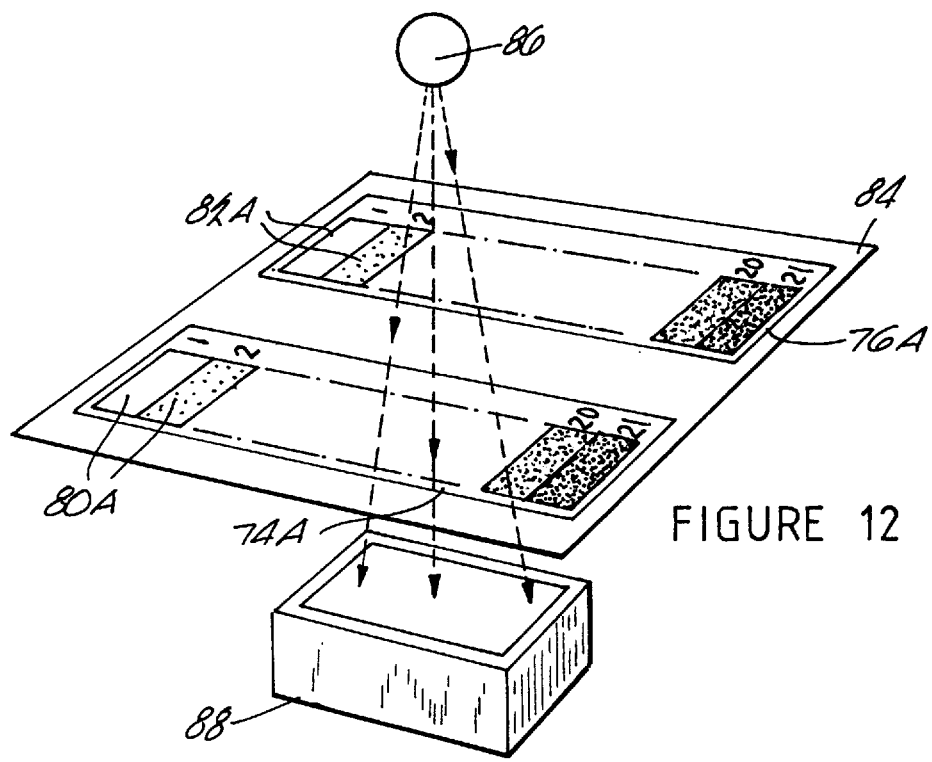

Referring to FIG. 12, there is shown a photograph 84, showing gray scale step wedges 74 and 76, acquired while the wedges were respectively illuminated as described above in connection with FIG. 11. Thus, photograph 84 depicts images 74A and 76A, respectively comprising the images of step wedges 74 and 76 which would be seen by the eye of a viewer (not shown) at the location of a camera (not shown) used to acquire the photograph 84. Images 74A and 76A respectively comprise images 80A and 82A of the corresponding steps 80 and 82. As is known to those of skill in the art, contrast between two adjacent regions of a film is defined as the difference between respective brightness or transmittance of light through the two regions, divided by the average transmittance therethrough. If T1 and T2 are the respective transmittances through each of two regions, and C12 is the contrast therebetween, the above relationship is stated mathematically as follows:

$$C_{12} = \frac{T_1 - T_2}{1/2(T_1 + T_2)} \qquad \text{Equation (1)}$$

Equation (1) was used to quantitatively demonstrate improvement in contrast between adjacent step images 82A of image 76A, associated with the film layers 78 of the invention, in comparison with prior art step images 80A. This was achieved by first measuring optical density for each of the step images 82A, and also for each of the step images 80A, respectively corresponding to gray scale wedge steps 7–12. The gray shades of such steps are radiologically usable. (The gray shades of steps 1–6 are generally too light to be of diagnostic value, and the shades 13–21 are too dark to be of diagnostic value.) Optical density was determined by sequentially projecting light from a light source 86 through respective step images 80A and 82A and measuring the respectively corresponding optical density values on a densitometer 88, such as a device manufactured by Tobias and Associates, Inc., and identified thereby as model TBX.

Table I shows respective optical density readings corresponding to gray scale steps 7–12 for both images 74A and 76A.

TABLE 1

| STEP | IMAGE 76A | IMAGE 74A |
|---|---|---|
| 7 | .41 | .41 |
| 8 | .43 | .42 |
| 9 | .49 | .46 |
| 10 | .61 | .56 |
| 11 | .90 | .79 |
| 12 | 1.67 | 1.37 |

As is known in the art, transmittance T through a region is related to the optical density O.D. by the following relationship:

$$O.D. = 1/\log T \qquad \text{Equation (2)}$$

It is to be understood that the logarithmic term in Equation (2) refers to log base ten. Applying equation 2 to respective values of optical density shown in Table I, the transmittance for each of the steps 7–13 of each of the images 76A and 74A is readily determined. Respective transmittance values therefore are set forth in Table II.

TABLE II

| STEP | IMAGE 76A | IMAGE 74A |
|---|---|---|
| 7 | .38904 | .38904 |
| 8 | .37153 | .38018 |
| 9 | .32359 | .34673 |
| 10 | .24547 | .27542 |
| 11 | .12589 | .16218 |
| 12 | .02137 | .04266 |

From Equation (1) and the transmittance values set forth in Table II, contrast can be readily calculated between steps 7 and 8, 8 and 9, 9 and 10, 10 and 11, and 11 and 12, for both images 74A and 76A. Such respective contrast values are set forth below, in Table III. Table III also shows the percentage of improvement in contrast between pairs of adjacent step images shown by image 76A, as compared with the corresponding step image pairs of image 74A. By averaging the improvement percentages shown in Table III, it is seen that the invention improves contrast over a prior art view box by an average of 37% for the five step wedge pairs represented in Table III.

TABLE III

| STEP | IMAGE 16A | IMAGE 74A | % IMPROV. |
|---|---|---|---|
| 7 to 8 | .0460444 | .023012 | 100% |
| 8 to 9 | .1379330 | .115018 | 19.9% |
| 9 to 10 | .274558 | .206468 | 33% |
| 10 to 11 | .644011 | .538976 | 19.5% |
| 11 to 12 | 1.419530 | 1.240389 | 14.4% |

To compare resolution provided by the invention with respect to a prior art view box, five radiologists, each certified by the American Board of Radiology, and certified in mammography by the American College of Radiology, and five registered radiologic technologists certified in mammography by the American College of Radiology, were each asked to view a film of the standard American College of Radiology mammography phantom as illuminated by a conventional prior art view box and also by a view box constructed in accordance with the embodiment of the invention shown in FIG. 6. Each of the radiologists and technologists concluded that resolution provided by such embodiment was significantly superior to the resolution provided by the prior art view box.

Obviously, many modifications and variations of the present invention are possible in light of the above teachings. For example, in one modification it is anticipated that the proportion of parallel light included in the total amount of film illuminating light could be increased only by refraction of light rays having angles of incidence exceeding the critical angle, as described above. In another modification, the same result could be achieved by only reflection. It is therefore to be understood that within the scope of the disclosed concept, the invention may be practiced otherwise than as specifically described.

What is claimed is:

1. Illuminating apparatus comprising:

a medical diagnostic imaging film supported in a specified plane;

means for projecting light comprising first and second portions toward said supported imaging film, said projected light having a first solid angle, said first and second portions including light rays directed at angles relative to said specified plane which are greater than, and less than, a critical angle, respectively; and light directing film means positioned between said light projecting means and said imaging film for refracting said first portion of projected light so that respective rays of said first portion are converged to lie within a second solid angle which is substantially less than said first solid angle, for directing said refracted first portion to illuminate said imaging film, and for selectively reflecting said second portion of projected light so that said reflected second portion does not illuminate said imaging film.

2. The apparatus of claim 1 wherein:

said apparatus includes means receiving said reflected second portion of projected light for preventing said reflected second portion from being transmitted to illuminate said imaging film.

3. The apparatus of claim 2 wherein:

said means for preventing transmission of said reflected second portion of projected light comprises a structure providing an interior space disposed to receive said reflected second portion.

4. The apparatus of claim 2 comprising:

means for supporting said imaging film in said specified plane.

5. The apparatus of claim 4 wherein:

said first solid angle is close to 180 degrees and said second solid angle is close to 90 degrees.

6. The apparatus of claim 4 wherein:

said light projecting means comprises a source of said projected light and a panel of selected material positioned between said imaging film and said microprism film.

7. The apparatus of claim 6 wherein:

said medical diagnostic imaging film comprises X-ray film.

* * * * *